United States Patent [19]

Yamada et al.

[11] Patent Number: 5,070,191

[45] Date of Patent: Dec. 3, 1991

[54] DEMETHYLALLOSAMIDIN AND A PROCESS FOR PRODUCTION THEREOF

[75] Inventors: Yasuhiro Yamada, Ikeda; Shohei Sakuda, Minoo; Seiji Takayama, Kawasaki, all of Japan

[73] Assignee: Ajinomoto Co., Inc., Tokyo, Japan

[21] Appl. No.: 515,703

[22] Filed: Apr. 27, 1990

[30] Foreign Application Priority Data

Apr. 27, 1989 [JP] Japan ................................. 1-105796

[51] Int. Cl.$^5$ ...................... C07H 19/00; C07H 21/00; C07D 263/58
[52] U.S. Cl. ......................................... 536/22; 435/84; 548/222; 514/27; 514/53; 536/4.1; 536/18.7; 536/53; 536/55
[58] Field of Search .................... 536/4.1, 53, 18.7, 55, 536/22; 514/27, 53; 548/222

[56] References Cited

PUBLICATIONS

Chemical Abstracts, vol. 109, No. 21, Nov. 21, 1988, Abstract 109:185939y.
Chemical Abstracts, vol. 109, No. 9, 8/29/88, Columbus, Ohio, U.S.A., Sakuda, Shohei et al., "Structures of Allosamidins, Novel Insect Chitinase Inhibitors Produced by Actinomycetes", p. 311, Abstract No. 69 316u & Agric. Biol. Chem. 1987, 51(12), 3251-9.
Chemical Abstracts, vol. 108, No. 15, 4/11/88, Columbus, Ohio, U.S.A., Sakuta, Shohei, "Specific Inhibito for Chitinase of Insects—Will It Be Available for Regulatory Controls in Insect Growth and Development", p. 348, Abstract No. 127 448f & Kagaku to Seibutsu, 1987, 25(12), 769-70.
The Journal of Antibiotics, vol. Xl, No. 3, Mar. 1987, Shohei Sakuda et al., "Search for Microbial Insect Growth Regulators II. Allosamidin, a Novel Insect Chitinase Inhibitor", pp. 296-300.
Chemical Abstracts, vol. 111, No. 9, 8/28/89, Columbus, Ohio, U.S.A., "Chitinase Activity from Candida Albicans and Its Inhibition by Allosamidin", pp. 333/334, Abstract No. 73 568m & J. Gen. Microbiol 1989, 135(6), 1417-21.

*Primary Examiner*—Ronald W. Griffin
*Attorney, Agent, or Firm*—Oblon, Spivak, McClelland, Maier & Neustadt

[57] ABSTRACT

An antifungal compound, demethylallosamidin, represented by the formula:

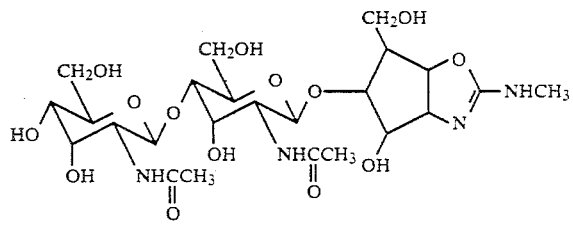

is disclosed. Methods of production and antifungal compositions comprising demethylallosamidin are also provided.

1 Claim, 1 Drawing Sheet

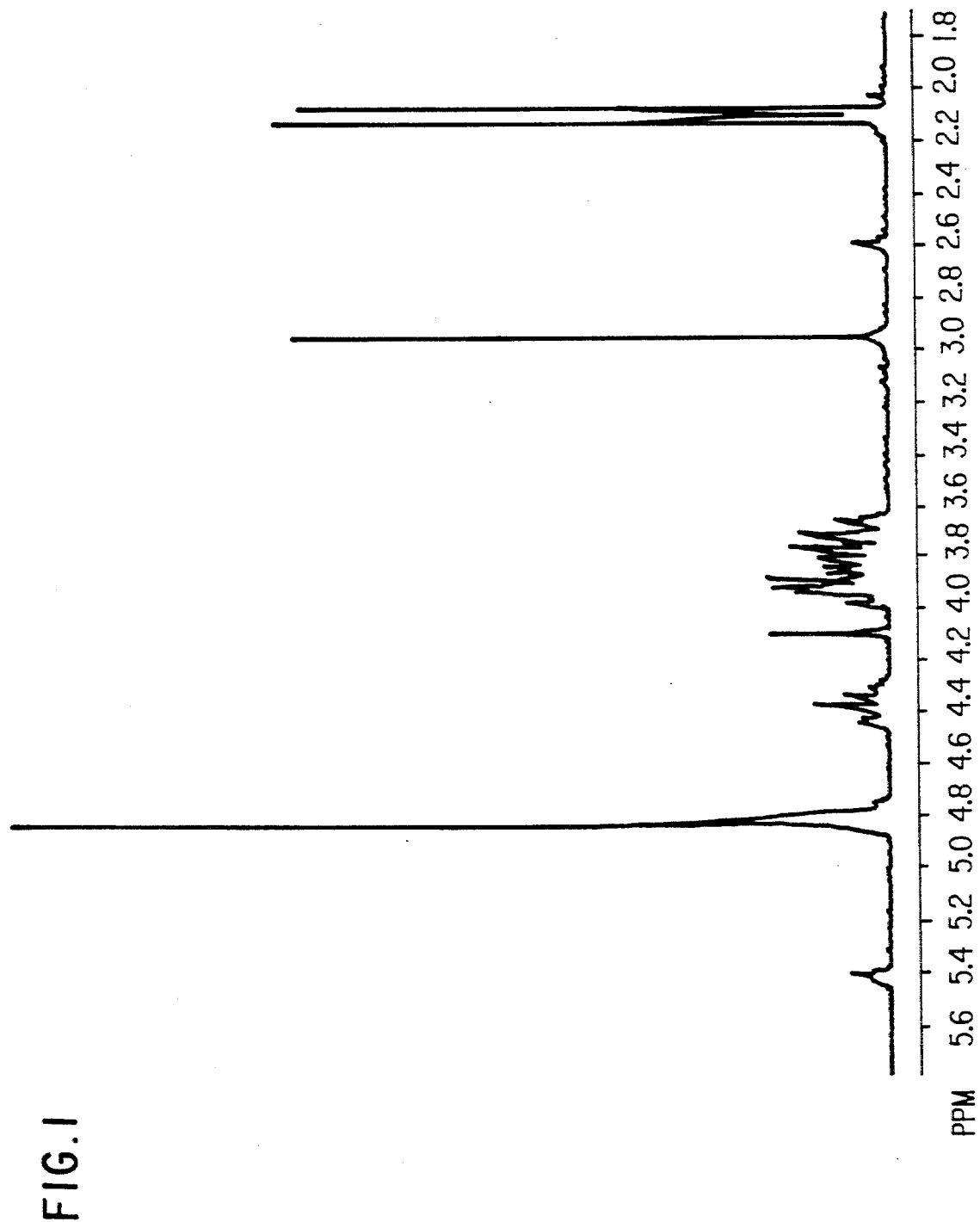
FIG. I

DEMETHYLALLOSAMIDIN AND A PROCESS FOR PRODUCTION THEREOF

BACKGROUND OF THE INVENTION

1. Field of the Invention

The present invention relates to novel allosamine derivatives and to an antifungal composition or chitinase inhibitor comprising the same as an effective ingredient.

2. Discussion of the Background

Chitin is the main component of the cell wall of fungi. G. W. Gooday and A. Trinci, Symposia of the Society for General Microbiology, 30, 207-251, (1980). It is believed that balanced synthesis and decomposition of chitin occurs during repeated division and proliferation of fungi. G. W. Gooday et al., "Chitin in Nature and Technology," pp. 83-91, Edited by R. A. A. Muzzarelli et al., Plenum Press, New York, (1986). On the other hand, chitin is the main component of the cuticule of insects and it is also known that synthesis and decomposition of chitin is subtly controlled during the course of ecdysis and growth of insects. K. J. Kramer et al., "Comprehensive Insect Physiology Biochemistry and Pharmacology" vol. 3, p. 75, Edited by G. A. Kerbut and L. I. Gilbert, Pergamon Press, Inc., New York, (1985).

It is known that biosynthesis and decomposition of chitin are regulated mainly by two enzymes: chitin synthase and chitinase, respectively. Thus, it is expected that inhibitors of these enzymes could lead to new types of antifungal agents or insect growth regulators (insecticide). In fact, polyoxin, which is an inhibitor of chitin synthase, has been used as an antifungal agent in agricultural applications. Inhibitory activity against ecdysis of insects was also reported in vivo. E. Cohen and J. E. Cashida, Pestic. Biochem, Physiol, 17, 301-306, (1982).

On the other hand, as inhibitors against chitinase, only allosamidin has been found heretofore. S. Sakuda et al., J. Antibiotics, 40, 296-300, (1987). Allosamidin strongly inhibits endo-type chitinase derived from insects and is thus expected to become a useful insecticidal or acaricidal agent. Japanese Patent Application Laid-Open No. 62-207294. However, allosamidin shows a weakly inhibitory activity against chitinase derived from fungi, so it is not an effective antifungal agent.

SUMMARY OF THE INVENTION

Accordingly, one object of the present invention is to provide a novel antifungal agent.

Another object is to provide a chitinase inhibitor.

Another object is provide an anti-fungal composition comprising demethylallosamidin as the active ingredient.

An object of this invention is to provide a process for producing demethylallosamidin from bacterial culture.

Another object is to provide a compound for the synthesis of a chitinase inhibitor, demethylallosamizoline.

BRIEF DESCRIPTION OF THE DRAWING

FIG. 1 is a drawing showing 'H-NMR spectrum of the compound of the present invention.

DETAILED DESCRIPTION OF THE PREFERRED EMBODIMENTS

The present inventors have made investigations of inhibitors against fungi-derived chitinase from naturally occurring substances. It has been discovered that the compound of formula (I), produced by a certain allosamidin-producing bacteria, exhibits extremely potent inhibitory activity.

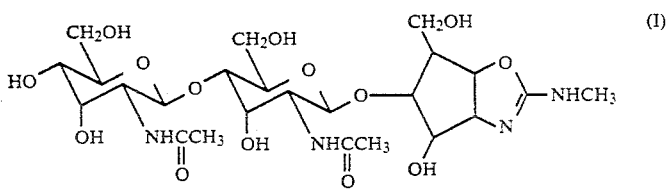

The compound of formula (I) has been named demethylallosamidin since it has the same structure as allosamidin except that one methyl group of the —N(CH$_3$)$_2$ group is missing, giving a —NHCH$_3$ group.

An example of a microorganism that is capable of producing demethylallosamidin is Streptomyces sp. AJ 9463 (FERM P-10642, FERM BP-2801). These bacteria grows aerobically in ISP3 medium used for identification of Actinomyces, form aerial mycelium, form no sporangium, and form but do not divide substrate mycelium. Substrate mycelium forms a long spore chain. Sporophore is not whirled. L,L-Diaminopimelic acid is contained in the cell wall. No characteristic sugar is present, and phospholipid is type PII. Based on the foregoing bacteriological properties, the strain has been identified as Streptomyces sp.

These bacteria are capable of producing demethylallosamidin and are useful for the large scale production of the compound. For example, Streptomyces sp., (FERM P-10642, FERM BP-2801) is cultured in an appropriate medium and demethylallosamidin is collected from the medium. A suitable method for culturing is similar to the culture of ordinary microorganisms, but deep culture in liquid medium is generally advantageous. Any medium may be usable for the culture, so long as it contains nutrient sources that the producing bacteria can utilize. For example, glucose, fructose, starch, dextrin, etc., are used as carbon sources. Suitable nitrogen sources are mused meat extract, casein, gluten, yeast extract, soybean powders, corn steep liquor, urea, ammonium sulfate, ammonium phosphate, etc. In addition, inorganic salts such as sodium hydrogenphosphate, magnesium sulfate, and calcium carbonate may be used if necessary. Where foaming is vigorous in culturing, a small quantity of silicone compounds, higher alcohols and vegetable oils, may be supplemented.

The temperature for the culture is advantageously between 20° and 35° C., most preferably at about 27° C. A time period for the culture is advantageously about 1 to 10 days but may be appropriately varied depending upon culture conditions.

Demethylallosamidin produced by the culture is accumulated mainly within the cells. Therefore in general, demethylallosamidin is isolated and purified from the cells by means of centrifugation, filtration, etc., in a manner conventionally used for isolation of ordinary antibiotics. The Isolation and purification may be carried out by solvent extraction with a lower alcohol such as methanol, ethanol, propanol n-butanol and by adsorption column chromatography on silica gel, diatomaceous earth, avicel, alumina, etc.; gel filtration using TOYO PEARL HW40 (carrier for gel filtration manufactured by Toyo Soda Mfg. Co., Ltd.), etc.; ion exchange chromatographies; reverse phase partition column chromatography and high performance liquid chromatography (HPLC) using octadodecylated (ODS) silica gel as a carrier. Furthermore, counter current partition, and other means for purification such as crystallization, recrystallization are used in appropriate combination.

Demethylallosamidin isolated and purified by these techniques exhibits a potent inhibitory activity against fungi-derived chitinase. The inhibitory activity of demethylallosamidin per unit weight is as much as 100 times that of allosamidin. Furthermore, cytotoxicity of demethylallosamidin is low. Demethylallosamidin showed no growth inhibition in mouse ascites mammary cancer cells or human leukemia cells at a dosage of 1 mg/ml.

Where demethylallosamidin of the present invention is utilized as an antifungal agent or chitinase inhibitor, the compound is prepared in pharmaceutically acceptable compositions that are conventionally used in preparations of antibiotics. The preparation is administered in the form of a solution, an emulsion, a suspension, a paste, powders, and the like.

Hydrolysis of demethylallosamidin under appropriate conditions, for example in 4 N hydrochloric acid at 100° C. for 4 hours, yield demethylallosamizoline having the following formula.

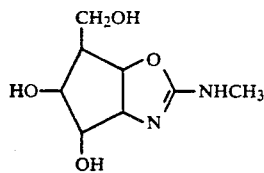

A big difference in inhibitory activity against fungal chitinase between demethylallosamidin and allosamidin is derived from this molecular piece. Thus, demethylallosamizoline is useful as a raw material for the synthesis of the present antifungal agent.

Other features of the invention will become apparent in the course of the following descriptions of exemplary embodiments which are given for illustration of the invention and are not intended to be limiting thereof.

Obviously, numerous modifications and variations of the present invention are possible in light of the above teachings. It is therefore to be understood that within the scope of the appended claims, the invention may be practiced otherwise than as specifically described herein.

EXAMPLES (1) Preparation of demethylallosamidin

A medium (pH 7.2) composed of glucose (12 g), meat extract (1.2 g), peptone (2.4 g), yeast extract (1.2 g) and water (1.2 liter) was prepared and 100 ml each of the medium was separately charged in 12 Erlenmeyer flasks having each volume of 500 ml, respectively.

After sterilization at 120° C. for 20 minutes, one platinum loop of slant cultured cells of Streptomyces sp. AJ 9463 (FERM P-10642, FERM BP-2801) was inoculated on each medium. Shake culture was carried out at 28° C. for 3 days to give seed mother liquor. On the other hand, 60 liters of medium having the composition described above was prepared and charged in a culture tank of 100 liter volume followed by sterilization at 120° C. for 30 minutes. To the medium was added 1.2 liter of the seed mother liquor described above followed by culturing at 27° C. for 5 days. During the culture, the agitation rate was 200 rpm and the air velocity was 60 liters/min. After celite was added to the thus obtained culture, the culture was filtered through a funnel to give a mixture of the cells and celite. Methanol (8 liters) was added to the mixture. After thoroughly stirring, the mixture was allowed to settle overnight. The mixture was filtered to give a methanol extract. The volume of extract was reduced to about 1 liter under reduced pressure, then distilled water was added to the residue to make the whole liquid volume 6 liters. The whole amount was adsorbed onto an activated charcoal column (volume of 600 ml). After washing the column with distilled water (1.8 liter), elution was performed sequentially with 10% ethanol (3 liters), 25% ethanol (3 liters) and 50% ethanol (3 liters). The activity was recovered mainly in the fraction eluted with 25% ethanol. After the fraction was concentrated to about 2 liters under reduced pressure, acetic acid was added to the concentrate to adjust the pH of the liquid to 3.8. The liquid was adsorbed onto SP-Sephadex C-25 cation exchange column (volume of 160 ml) equilibrated with 50 mM ammonium acetate/acetic acid (pH 5.0). One step elution was performed with the same buffer to fractionate by 8 ml each. With respect to each fraction, the activity was determined and fractionated into two fractions: Fraction Nos. 55 to 64 having a weak specific activity and Fraction Nos. 65 to 75 having a strong specific activity. Among them, it was found that the active component of Nos. 55 to 64 was allosamidin, based on various physicochemical properties such mass spectrosopy (FABMS), and nuclear magnetic resonance (NMR).

Fraction Nos. 65 to 75 were desalted with a small quantity of activated charcoal then concentrated under reduced pressure and finally purified by high performance liquid chromatography (moving phase: 10 mM ammonium acetate/ammonia (pH 8.9), flow rate=1.0 ml/min) using weakly cationic exchange column Asahipak ES-502C. Detection was made by UV absorption at 220 nm and two peaks showing retention time (tR) of 7.0 minutes and 8.8 minutes were fractionated and freeze-dried. Among them, the substance having tR of 8.8 minutes was identified as allosamidin, based on various physicochemical properties. The other substance, showing tR of 7.0 minutes, was identified as demethylallosamidin, which gives a single peak on HPLC using various ion exchange columns. Its identification is based on various physicochemical properties described below.

(1) Appearance: white powder
(2) Molecular formula: $C_{24}H_{40}N_4O_{14}$
(3) FABMS: m/z 609 (M+H)+, glycerol matrix (4) UV absorption spectrum: terminal absorption (in 0.1 N acetic acid)
(5) $^1$H-NMR spectrum: as shown in FIG. 1 (600 MHz, D$_2$O+AcOD)

(2) Determination of chitinase inhibitory activity of demethylallosamidin

Demethylallosamidin of formula (I) prepared as described above had a potent inhibitory activity against fungi-derived chitinase.

(i) Preparation of chitinase solution

A Sakaguchi flask of 2 liters was charged with 1 liter of 25 mM MES (Nakarai Chemical Co., Ltd.) buffer containing 0.1% β-mercaptoethanol and 200 g of baker's yeast (Kanegafuchi Chemical Industry Co., Ltd.) followed by shaking at 30° C. at 120 spm for 2 hours. The cells were removed by centrifugation (0° C., 10 mins., 12,000 g). The resulting supernatant was concentrated to 200 ml by ultrafiltration (TOYO ULTRA-FILTER UP-20). After concentration, 400 ml of citrate buffer (0.15 M citric acid+0.15 M sodium citrate, pH 3.0) was added to the concentrate. After the formed precipitates were removed by centrifugation (0° C., 10 mins., 12,000 g), the resulting supernatant was concentrated to 40 ml by ultrafiltration. The concentrate was stored at 4° C. and used as the chitinase solution in the assay.

(ii) Preparation of enzyme substrate 10 ml of 10% acetic acid was slowly added to 0.5 g of chitosan (PFANSTIEHL LABORATORIES INC.), then the mixture was kneaded in a mortar to become gel-like. After standing at room temperature overnight, 45 ml of methanol was added while thoroughly stirring. The mixture was filtered through a gauze and 0.75 ml of $^3$H-labeled acetic anhydride (NET 018A10 ACETIC ANHYDRIDE 5 mCi) was added to the filtrate obtained. The formed agar-like chitin was homogenized with a homogenizer, collected on a glass filter (Whatmann GF/B) and suspended in 10 ml of citrate buffer (pH 3.0). This chitin suspension (2.3 μCi/ml chitin suspension) was used as a substrate for assay.

(iii) Method for determination of chitinase inhibitory activity

In an Epfendorf tube, 90 μl of the chitinase solution and 10 μl of the $^3$H-chitin suspension were charged and reacted at 37° C. for 3 hours. In this case, 90 μl of citrate buffer (pH 3.0) was used in place of 90 μl of the enzyme solution as a control sample and reacted in a similar manner. After the reaction, 100 μl of 10% trichloroacetic acid was added and the reaction solution was passed through a glass filter (Whatmann GF/B). After 10 ml of scintillant solution was added to the obtained filtrate, its radioactivity (dpm) was determined. The difference between the determined value and the control sample indicated chitinase activity. The scintillant solution was prepared by dissolving 4 g of Ominiflour (Daiichi Chemical) in 500 ml of toluene and adding 500 ml of Triton X-100 (Nakarai Chemical Co., Ltd.) to the solution.

When allosamidin and demethylallosamidin were added, both were dissolved in 0.1 N acetic acid solution and 10 μl each of the solutions having the respective concentrations was added to the reaction system described above. Also, 10 μl of 0.1 N acetic acid was added to the blank and to the system in which no inhibitor was added, followed by the reaction described above.

The inhibitory activity was calculated according to the equation below:

$$\text{Inhibitory activity (\%)} \left[ \frac{A - B}{A} \right] \times 100$$

wherein:
A=chitinase activity (dpm) when no inhibitor was added.
B=chitinase activity (dmp) when the inhibitor was added.

In any of the measurements, three series of runs were used and a mean value was determined.

(iv) Results

The results are as shown in Table 1.

TABLE 1

|  |  | Inhibition Rate (%) |
|---|---|---|
| No inhibitor |  | 0 |
| Demethylallosamidin |  |  |
| Amount added | 0.8 μg | 87.1 |
|  | 0.4 μg | 84.6 |
|  | 0.2 μg | 75.2 |
|  | 0.1 μg | 73.9 |
|  | 0.05 μg | 61.1 |
| Allosamidin |  |  |
| Amount added | 4 μg | 58.5 |
|  | 2 μg | 47.6 |
|  | 1 μg | 36.0 |

(3) Influence of demethylallosamidin on growth of mold

Demethylallosamidin was added to the culture medium of mold to examine its influence. Firstly, *Fusarium nivale* ATCC 42308 was precultured in PDA medium (manufactured by Nissui Pharmaceutical Co., Ltd.) to form spores. The spores were suspended in physiological saline. The suspension was filtered through cotton to give a spore suspension free of hyphae.

A fixed amount of the resulting suspension was inoculated on a medium supplemented with demethylallosamidin (0.80 μg/ml, 0.16 μg/ml) and on demethylallosamidin-free medium (control), respectively. Change in subsequent incubation was observed with passage of time. The observation was performed as follows: sampling was made over definite periods of time, microscopic photographs were taken and the length and branching degree of hyphae were determined. The branching degree of hyphae is a mean value of branch intervals of hyphae. In any case, incubation was carried out at 28° C. at 120 strokes/min by charging 1 ml each of medium (0.03% of yeast extract, 0.03% of malt extract; both manufactured by Daigo Nutrient Co., Ltd.) and 0.1% of glucose in a testing tube with a cotton stopper (diameter of 11 mm).

The length and branching degree of hyphae after 32 hours are as shown in Table 2. That is, by the addition of demethylallosamidin, the length of hyphae obviously increased and the branching degree decreased. Particularly at the top of hyphae, decrease in the branching degree was remarkable.

TABLE 2

| Concentration of Demethylallosamidin (μg/ml) | Length Hypha (μg) | Branching Degree of Hypha (μm) |
|---|---|---|
| 0 | 143 | 49.2 |
| 0.16 | 364 | 72.8 |

TABLE 2-continued

| Concentration of Demethylallosamidin (μg/ml) | Length Hypha (μg) | Branching Degree of Hypha (μm) |
| --- | --- | --- |
| 0.80 | 576 | 74.2 |

(4) Cytotoxicity of demethylallosamidin (i) Mouse ascitic mammary cancer cells FM3A were inoculated in $1 \times 10^5$/ml on Dulbecco modified MEM medium supplemented with 10% fetal calf serum and demethylallosamidin was added thereto in a concentration of 1 mg/ml followed by stationary culture at 37° C. for 4 days. Microscopic observation of the cultured mouse ascitic mammary cancer cells FM3A reveal that no growth inhibition was noted at all.

(ii) Human leukemia cells K562 were inoculated in $1 \times 10^5$/ml on FRMI 1640 medium supplemented with 10% fetal calf serum and demethylallosamidin was added thereto in a concentration of 1 mg/ml followed by stationary culture at 37° C. for 4 days. Microscopic observation of the cultured human leukemia cells K562 reveal that no growth inhibition was noted at all.

The compound of the present invention has an extremely potent inhibitory activity against fungi-derived chitinase. Accordingly, an antifungal agent and chitinase inhibitor having excellent pharmaceutical effects are provided. In addition, this compound can be produced by fermentation and is thus produced in large quantities.

What is claimed as new and desired to be secured by Letters Patent of United States is:

1. The compound represented by the following formula:

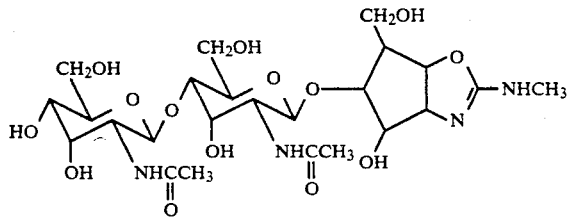

UNITED STATES PATENT AND TRADEMARK OFFICE
CERTIFICATE OF CORRECTION

PATENT NO. : 5,070,191

DATED : December 3, 1991

INVENTOR(S) : Yasuhiro Yamada, et al.

It is certified that error appears in the above-identified patent and that said Letters Patent is hereby corrected as shown below:

On the title page:

The second Priority Data has been omitted, should be,

--Mar. 23, 1990 [JP]   Japan   2-71972--.

Signed and Sealed this

Twenty-seventh Day of April, 1993

*Attest:*

MICHAEL K. KIRK

*Attesting Officer*   Acting Commissioner of Patents and Trademarks

UNITED STATES PATENT AND TRADEMARK OFFICE
CERTIFICATE OF CORRECTION

PATENT NO. : 5,070,191

DATED : DECEMBER 3, 1991

INVENTOR(S) : YASUHIRO YAMADA ET AL

It is certified that error appears in the above-identified patent and that said Letters Patent is hereby corrected as shown below:

Column 1, line 64, after "is", insert --to--.

Signed and Sealed this

Twentieth Day of July, 1993

Attest:

MICHAEL K. KIRK

Attesting Officer

Acting Commissioner of Patents and Trademarks